United States Statutory Invention Registration [19]

[11] Reg. Number: H448

Farncomb et al. [43] Published: Mar. 1, 1988

[54] CO-NITRATION OF 1,2,4-BUTANETRIOL AND GLYCERIN

[75] Inventors: Robert E. Farncomb, Accokeek; Walter A. Carr, Oxon Hill, both of Md.

[73] Assignee: The United States of America as represented by the Secretary of the Navy, Washington, D.C.

[21] Appl. No.: 70,758

[22] Filed: Jul. 6, 1987

[51] Int. Cl.[4] ..... C06B 25/14; C07C 76/04

[52] U.S. Cl. ..... 149/104; 149/88; 558/484; 558/486; 260/688

*Primary Examiner*—John F. Terapane
*Assistant Examiner*—J. E. Thomas
*Attorney, Agent, or Firm*—Kenneth E. Walden; Roget D. Johnson

[57] ABSTRACT

A process for preparing an energetic mixture of 1,2,4-butanetroil trinitrate and nitroglycerin by forming a polyol mixture of 1,2,4-butanetriol and glycerin, and then nitrating the polyol mixture with a mixture of nitric and sulfuric acids.

6 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CO-NITRATION OF 1,2,4-BUTANETRIOL AND GLYCERIN

BACKGROUND OF THE INVENTION

This invention relates to nitrate esters and more particularly to methods of co-nitrating polyols to produce nitrate ester mixtures.

Mixtures of 1,2,4-butanetriol trinitrate and nitroglycerin are useful as energetic components in explosives and gun propellants. Normally, 1,2,4-butanetriol and glycerin are nitrated separately to form 1,2,4-butanetriol trinitrate and nitroglycerin which are then blended together in the desired proportions. This requires that one of the nitrate esters be stored while the other is being made. This storage is undesirable because either nitroglycerin or 1,2,4-butanetriol trinitrate is more sensitive to impact than a blended mixture of the two. Moreover, fume-offs frequently occur during the nitration of 1,2,4-butanetriol alone. It would be desirable to provide a method of reducing or eliminating these problems.

SUMMARY OF THE INVENTION

Accordingly, an object of this invention is to provide a new method of producing mixtures of 1,2,4-butanetriol trinitrate and nitroglycerin.

Another object of this invention is to provide a safer method of producing mixtures of 1,2,4-butanetriol trinitrate and nitroglycerin.

A further object of this invention is to avoid fume-offs during the preparation of mixtures of 1,2,4-butanetriol trinitrate and nitroglycerin.

These and other objects of this invention are accomplished by providing a process for preparing an energetic binary mixture of 1,2,4-butanetriol trinitrate and nitroglycerin by:

a. forming a binary polyol mixture of from about 40 to about 60 weight percent of 1,2,4-butanetriol with the remainder of the polyol mixture being glycerin;

b. nitrating the polyol mixture with a mixed acid of from 30 to 60 weight percent of nitric acid with the remainder of the mixed acid being sulfuric acid; and c. isolating the product mixture of 1,2,4-butanetriol trinitrate and nitroglycerin.

DETAILED DESCRIPTION OF THE PREFERRED EMBODIMENT

It is critical that the 1,2,4-butanetriol, $HOCH_2CH(OH)CH_2CH_2OH$, and glycerin, $HOCH_2CH(OH)CH_2OH$, starting materials be thoroughly mixed prior to the nitration step. In this way fuming off (of nitric acid), which frequently occurs in the normal nitration of 1,2,4-butanetriol, is avoided. Preferably from about 40 to about 60 and more preferably from 50 to 55 weight percent of 1,2,4-butanetriol is used, with glycerin being the remainder of the polyol mixture.

A mixed acid containing from 30 to 60 weight percent of nitric acid with the remainder being sulfuric acid is used as the nitrating agent. A more preferred mixed acid will contain from 38 to 42 weight percent of nitric acid with the remainder being sulfuric acid.

The amount of mixed acid used will preferably provide an excess of from 30 to 50 percent of nitric acid based on the stoichiometric amount calculated for the complete conversion of 1,2,4-butanetriol and glycerin to 1,2,4-butanetriol trinitrate g and nitroglycerin. More preferably an excess of from 40 to 44 percent of nitric acid is used.

Preferably the polyol mixture is fed into the mixed acid with vigorous agitation (e.g., stirring) of the mixed acid to prevent hot spots. Agitation of the reaction mixture is continued during the nitration step. The nitration reaction is exothermic and conventional methods such as rate of polyol feed and external cooling are used to control the reaction temperature. Preferably the reaction temperature is kept in the range of from 5° C. to 20° C. Below 5° C. certain reactants may freeze and separate from the reaction mixture. Temperatures above 20° C. may result in the decompostion of the products.

The product 1,2,4-butanetriol trinitrate/nitroglycerin mixture separates as a clear oil from the spent acid phase. There is no stable oil/water emulsion formed. This contrasts with the nitration of glycerin alone in which some stable emulsion of nitroglycerin and water is usually formed.

As illustrated in the examples, the product 1,2,4-butanetriol trinitrate/nitroglycerin oil mixture is washed first with a weak aqueous base and then with water to remove traces of the acids.

To more clearly illustrate this invention, the following examples are presented. It should be understood, however, that these examples are presented merely as a means of illustration and are not intended to limit the scope of the invention in any way.

EXAMPLE 1

46.6 grams of a binary solution of 53.1 weight percent of 1,2,4-butanetriol (96 percent pure) and 46.9 weight percent of glycerin at 41° C. was pumped into 300 grams of mixed acid (38.1 weight percent of nitric acid and 58.8 weight percent of sulfuric acid) at 15±1° C. This is a 43 percent excess of nitric acid. During the nitration the mixture was agitated with a high-speed, high-shear mixer. During the nitration the change in redox was 80 mv. (A sample of this 1,2,4-butanetriol nitrated by itself had a change in redox of 130 mv.) The nitration mixture was drowned in 1000 grams of 6° C. water with a 18° C. temperature rise. The calculated spent acid analysis was:

| | |
|---|---|
| % Nitric Acid | 11.8 |
| % Sulfuric Acid | 71.8 |
| % Oxides | 0.5 |
| % Water assuming 1% NG and 1% BTTN | 13.9 |
| $H_2O/H_2SO_4$ Mole Ratio | 1.05 |

The 1,2,4-butanetriol trinitrate (BTTN)/nitroglycerin (NG) mixture at 35° to 40° C. was washed four times with 300 ml of 13 percent sodium carbonate and 3 times with water. Each wash was agitated for 15 minutes with the high-speed, high-shear agitator. The results of the BTTN-NG analysis are:

| | | |
|---|---|---|
| % BTTN | 52.1 | |
| % NG | 46.9 | |
| KI heat test min | 18 | 10 min minimum |
| % water | 0.1 | |
| % N | 17.9 | |
| pH | Neutral | |

EXAMPLE 2

The same as Example 1 except that a binary mixture of 52.07 weight percent of 1,2,4-butanetriol (99.8 percent pure) and 47.93 weight percent of glycerin was pumped into the mixed acid at a rate of 3.3 grams per minute. The change in redox was 49 mv. (A sample of this 1,2,4-butanetriol nitrated by itself had a change of redox of 58 mv.) The 1,2,4-butanetriol trinitrate (BTTN)/nitroglycerin (NG) mixture was separated from the spent acid. The results of the spent acid analysis were:

| | |
|---|---|
| % Nitric Acid | 9.16 |
| % Sulfuric Acid | 75.68 |
| % Oxide | 0.64 |
| % Water (calculated) | 11.6 |
| $H_2O/H_2SO_4$ Mole Ratio | 0.86 |

The results of BTTN-NG analysis were:

| | |
|---|---|
| KI heat test | 8.7 min |
| % BTTN | 50.9 |
| % NG | 49.1 |

To those skilled in the art, many modifications and variations of the present invention are possible in light of the above teachings. It is therefore to be understood that the present invention can be practiced otherwise than as specifically described herein and still be within the scope of the appended claims.

What is claimed is:

1. A process for preparing an energetic binary mixture of 1,2,4-butanetriol trinitrate and nitroglycerin comprising:

a. forming a binary polyol mixture consisting essentially of from about 40 to about 60 weight percent of 1,2,4-butanetriol with the remainder of the polyol mixture being glycerin;

b. nitrating the polyol mixture with a mixed acid consisting essentially of from 30 to 60 weight percent of nitric acid with the remainder of the mixed acid being sulfuric acid; and c. isolating the product mixture of 1,2,4-butanetriol trinitrate and nitroglycerin.

2. The process of claim 1 wherein the binary polyol mixture consists essentially of from 50 to 55 weight percent of 1,2,4-butanetriol with the remainder of the polyol mixture being glycerin.

3. The process of claim 1 wherein the nitration temperature is maintained in the range of from 5° C. to 20° C. during step (b).

4. The process of claim 1 wherein the mixed acid consists essentially of from 38 to 42 weight percent of nitric acid with the remainder of the mixed acid being sulfuric acid.

5. The process of claim 1 wherein the amount of mixed acid used in step (b) provides a 30 to 50 percent excess of nitric acid over the stoichiometric amount calculated for the complete nitration of the 1,2,4-butanetriol and glycerin.

6. The process of claim 5 wherein the amount of mixed acid used in step (b) provides a 40 to 44 percent excess of nitric acid over the stoichiometric amount calculated for the complete nitration of the 1,2,4-butanetriol and glycerin.

* * * * *